United States Patent [19]

Takago et al.

[11] Patent Number: 4,539,418

[45] Date of Patent: Sep. 3, 1985

[54] METHOD FOR THE PREPARATION OF PENTAMETHYLCYCLOTRISILOXANE

[75] Inventors: Toshio Takago; Masatoshi Arai, both of Gunma, Japan

[73] Assignee: Shin-Etsu Chemical Co., Ltd., Tokyo, Japan

[21] Appl. No.: 672,412

[22] Filed: Nov. 16, 1984

[30] Foreign Application Priority Data

Nov. 28, 1983 [JP] Japan .................................. 58-223499

[51] Int. Cl.$^3$ ................................................. C07F 7/08
[52] U.S. Cl. ....................................... 556/451; 556/460
[58] Field of Search ................................. 556/451, 460

[56] References Cited

U.S. PATENT DOCUMENTS

| 2,595,891 | 5/1952 | Sauer ..................................... 556/451 |
| 3,234,180 | 2/1966 | Wu ..................................... 556/451 X |
| 3,317,578 | 5/1967 | Prescott et al. ................. 556/460 X |
| 3,576,023 | 4/1971 | Curry ..................................... 556/451 |
| 3,714,213 | 1/1973 | Miller et al. ......................... 556/451 |
| 4,412,080 | 10/1983 | Williams .............................. 556/460 |

FOREIGN PATENT DOCUMENTS 410023  1/1974  U.S.S.R. .............................. 556/451

*Primary Examiner*—Paul F. Shaver
*Attorney, Agent, or Firm*—Toren, McGeady, Stanger, Goldberg & Kiel

[57] ABSTRACT

A very efficient method is proposed for the synthetic preparation of pentamethylcyclotrisiloxane by the ring-closing reaction between 1,1,3,3-tetramethyl-1,3-dihydroxy disiloxane and a methyl dialkenyloxysilane such as methyl diisopropenyloxysilane at a moderate temperature in a solution with an organic solvent.

4 Claims, No Drawings

METHOD FOR THE PREPARATION OF PENTAMETHYLCYCLOTRISILOXANE

BACKGROUND OF THE INVENTION

The present invention relates to a method for the synthetic preparation of pentamethylcyclotrisiloxane.

Pentamethylcyclotrisiloxane is an important basic material in the formulation of certain types of silicone rubbers. For example, the silicon-bonded hydrogen atom in the molecule of the cyclotrisiloxane is reactive with an ethylenically unsaturated linkage so that pentamethylcyclotrisiloxane is subjected to addition reaction with a linear organopolysiloxane having ethylenically unsaturated bonds in both molecular chain ends in the presence of a catalyst to form an organopolysiloxane having a pentamethyltrisiloxane ring at each of the molecular chain ends which is then subjected to a reaction of ring-opening polymerization in the presence of another catalyst to produce crosslinks between the organopolysiloxane molecules so as to impart the organopolysiloxane with rubbery elasticity.

In the prior art, no method for the direct synthesis of pentamethylcyclotrisiloxane is known and this compound is obtained only as a minor byproduct in the preparation of methylpolysiloxanes by the hydrolysis of methyl chlorosilanes followed by the distillation of the hydrolysis product. Therefore, pentamethylcyclotrisiloxane is available only in a very limited amount.

Turning now to the preparation method of cyclotrisiloxane compounds in general, a method is proposed in Japanese Patent Publication No. 43-14720 in which a dichlorosilane compound and a 1,3-dihydroxy-substituted disiloxane compound are reacted in the presence of an acid acceptor such as an amine compound. This method is, however, not quite satisfactory from the industrial point because the reaction procedure is very complicated including the filtration to separate the salt as a by-product and chilling of the reaction mixture to ensure a good yield of the desired cyclotrisiloxane. Moreover, this method is less applicable to the preparation of pentamethylcyclotrisiloxane as the subject material of the present invention because this particular cyclotrisiloxane is susceptible to decomposition by the reaction with the hydrochloride as the by-product and the dichlrosilane compound as the starting material remaining in the reaction mixture so that the yield of the desired compound can never be high enough.

SUMMARY OF THE INVENTION

It is therefore an object of the present invention to provide a novel and efficient method for the synthetic preparation of pentamethylcyclotrisiloxane without the problems in the prior art method for the synthesis of cyclotrisiloxane compounds in general in a simple reaction procedure and in a very high yield of the desired compound.

Thus, the method of the present invention for the synthetic preparation of pentamethylcyclotrisiloxane comprises mixing 1,1,3,3-tetramethyl-1,3-dihydroxydisiloxane and a methyl dialkenyloxysilane represented by the general formula

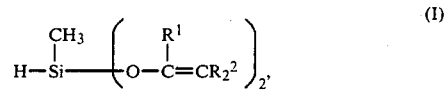

in which $R^1$ is an alkyl group having 1 to 4 carbon atoms and each $R^2$ is a hydrogen atom or an alkyl group having from 1 to 4 carbon atoms independently from the other to effect the reaction between these two types of the organosilicon compounds.

Advantageously and differently from the reaction mixture in the prior art method for the preparation of cyclotrisiloxane compounds in general, the reaction mixture in the above described inventive method is neutral so that the once formed pentamethylcyclotrisiloxane is safe from the decomposition reaction by the acidic constituents in the reaction mixture to be isolated and purified with stability. Therefore, the desired cyclotrisiloxane product can be obtained in a high yield in addition to the advantage of the simple and easy reaction procedure as a result of the readily proceeding ring-closing reaction in the reaction system.

DETAILED DESCRIPTION OF THE PREFERRED EMBODIMENTS

One of the starting reactants pertaining to the reaction of the inventive method is a methyl dialkenyloxysilane compound represented by the above given general formula (I). In the general formula, the symbol $R^1$ denotes an alkyl group having from 1 to 4 carbon atoms including methyl, ethyl, propyl and butyl groups and each of the two $R^2$ groups is a hydrogen atom or an alkyl group having 1 to 4 carbon atoms including methyl, ethyl, propyl and butyl groups independently from the other. Several of the particular examples of the methyl dialkenyloxysilane compound of the general formula are the compounds expressed by the following structural formulas:

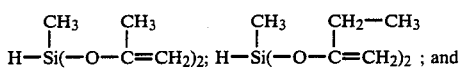

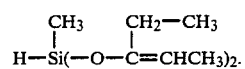

In the method of the present invention, 1 mole of the methyl dialkenyloxysilane compound is reacted with 1 mole of 1,1,3,3-tetramethyl-1,3-dihydroxydisiloxane to form 1 mole of the desired pentamethylcyclotrisiloxane by the ring-closing reaction. In practice, the reaction mixture should contain from 0.8 to 1.2 moles of the disiloxane per mole of the silane compound. Since the disiloxane is a crystalline solid at room temperature, it is convenient that the disiloxane compound is dissolved or dispersed in a suitable organic solvent and the solution or dispersion is admixed with the silane compound. Examples of the organic solvent suitable for the purpose include aromatic and aliphatic hydrocarbon solvents such as toluene, xylene, n-hexane and the like, chlorinated hydrocarbon solvents such as methylene chloride, carbon tetrachloride and the like and ether solvents such as diethyl ether, dibutyl ether and the like. The amount of the organic solvent should be in the range from 50 to 1000 parts by weight or, preferably, from 100 to 500 parts by weight per 100 parts by weight of the disiloxane compound.

As is mentioned above, the reaction of the inventive method can be performed by adding the silane compound dropwise into a solution or dispersion of the disiloxane compound in an organic solvent. The reaction can proceed at a relatively low temperature and the reaction temperature should be in the range from −10° to +80° C. or, preferably, from 0° to +50° C. When the temperature is too low, the reaction velocity is unduly low while, when the temperature is excessively high over 80° C., the yield of undesirable byproducts is disadvantageously increased. The reaction between the silane compound and the disiloxane compound is an exothermic reaction so that the temperature of the reaction mixture immediately begins to increase when the dropwise addition of the silane compound to the reaction mixture is started. It is, however, not always necessary to take a cooling measure unless the temperature of the reaction mixture exceeds the above mentioned upper limit of the temperature range. No heating means is also required usually with an object to accelerate the reaction by increasing the temperature of the reaction mixture.

The ring closing reaction between the silane compound and the disilocane compound can proceed even in the absence of a catalyst but the reaction velocity can be somewhat increased by the addition of a suitable catalyst to the reaction mixture. Useful catalysts for the purpose include metal salts of carboxylic acids such as lead 2-ethylhexoate, dibutyltin dioctoate, dibutyltin diacetate, dibutyltin dilaurate, iron 2-ethylhexoate, cobalt 2-ethylhexoate, tin(II) caprylte, tin naphthenate, tin butyrate, titanium naphthenate, cobalt naphthenate and zinc stearate, organic titanate esters such as tetrabutyl titanate, tetra-2-ethylhexyl titanate and trimethanolamine titanate, organic titanium compounds such as organosiloxy titanium compounds and β-carbonyl titanium, alkoxy aluminum compounds, amine compounds and salts thereof such as 3-aminopropyl triethoxysilane, hexylamine and dodecyl phosphate amine complexes, quaternary ammonium salts such as benzyl triethyl ammonium acetate, alkali metal salts of lower carboxylic acids such as potassium acetate, sodium acetate and lithium oxalate, dialkyl hydroxylamine compounds such as dimethyl hydroxylamine and diethyl hydroxylamine, guanidino group containing organosilicon compounds, i.e. organosilane and organopolysiloxane compounds, expressed by the chemical formulas, denoting a methyl group by the symbol Me:

$$(Me_2N)_2—C=N(CH_2)_3Si(OMe)_3;$$

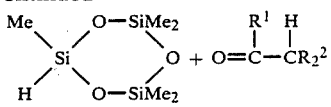

and the like.

The reaction of the inventive method proceeds presumably according to the following reaction equation

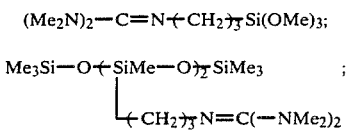

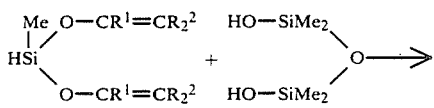

to produce an aldehyde or ketone compound as the byproduct when $R^1$ is a hydrogen atom or an alkyl group, respectively. Such a byproduct compound is not reactive with the desired product of pentamethylcyclotrisiloxane so that the byproduct compound never acts to decrease the yield of the desired product which can be easily purified and isolated by distillation under normal or reduced pressure to remove the byproduct compound and the unreacted reactant compounds.

In the following, the method of the present invention is described in more detail by way of examples.

EXAMPLE 1

Into a glass-made flask of 200 ml capacity equipped with a stirrer and a thermometer were introduced 30 g (0.18 mole) of 1,1,3,3-tetramethyl-1,3-dihydroxy disiloxane and 30 g of methylene chloride and the disiloxane was dispersed in the solvent with agitation. Then, 28.6 g (0.18 mole) of methyl diisopropenyloxy silane were added dropwise into the reaction mixture in the flask under continued agitation over a period of 30 minutes. As the silane compound is added, the turbidity of the dispersion in the flask gradually decreased and the reaction mixture was clear at the completion of the dropwise addition of the silane compound indicating a reaction taking place between the disiloxane and the silane. The temperature of the reaction mixture increased from 18° C. before the addition of the silane compound to 35° C. after completion thereof.

After completion of the dropwise addition of the silane compound, the reaction mixture was further agitated for addition-al 1 hour keeping the temperature at 35° C. to complete the reaction and then distilled under reduced pressure to strip the methylene chloride as the solvent and acetone formed as a byproduct followed by distillation under reduced pressure to give 16.0 g of pentamethylcyclotrisiloxane boiling at 32° C. under a pressure of 25 mmHg and having a refractive index of 1.3807 at 20° C. The yield of this product was 42.6% of the theoretical value calculated from the amount of the isopropenyloxy silane.

EXAMPLE 2

The experimental procedure was substantially the same as in Example 1 excepting the use of 33.5 g (0.18 mole) of the methyl dialkenyloxysilane of the formula

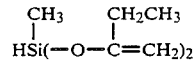

in place of 16.0 g of methyl diisopropenyloxysilane used in Example 1. The yield of the desired product pentamethylcyclotrisiloxane was 14.5 g.

EXAMPLE 3

The experimental procedure was substantially the same as in Example 1 excepting the use of 38.6 g of the methyl dialkenyloxy silane of the formula

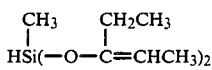

in place of 16.0 g of methyl diisopropenyloxy silane and 30 g of diethyl ether in place of 30 g of methylene chloride each used in Example 1. The yield of pentamethylcyclotrisiloxane was 15.3 g.

COMPARATIVE EXAMPLE

A solution prepared by dissolving 16.6 g of 1,1,3,3-tetramethyl-1,3-dihydroxy disiloxane in 39 g of diethyl ether and another solution prepared by dissolving 11.5 g of methyl dichlorosilane in 39 g of diethyl ether were introduced dropwise separately but simultaneously into a mixture of 19.3 of triethylamine and 129 g of diethyl ether in in a flask of 500 ml capacity through respective dropping funnels at such uniform rates that addition of the two solutions was completed within 30 minutes. The temperature of the reaction mixture was kept at 0° to 5° C. throughout the addition of the solutions.

After completion of the dropwise addition of the solutions, agitation was further continued for additional 1 hour to complete the reaction followed by filtration to remove the hydrochloride of the amine and stripping of diethyl ether under reduced pressure. Distillation of the resultant reaction mixture under reduced pressure gave only 2.5 g of pentamethylcyclotrisiloxane corresponding to 6.7% of the theoretical value.

What is claimed is:

1. A method for the synthetic preparation of pentamethylcyclotrisiloxane which comprises: admixing 1,1,3,3-tetramethyl-1,3-dihydroxy disiloxane and a methyl dialkenyloxysilane represented by the general formula

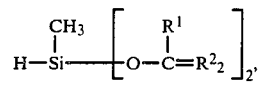

in which $R^1$ is an alkyl group having from 1 to 4 carbon atoms and $R^2$ is a hydrogen atom or an alkyl group having from 1 to 4 carbon atoms to effect ring-closing reaction.

2. The method as claimed in claim 1 wherein 1 mole of the methyl dialkenyloxysilane is admixed with 0.8 to 1.2 moles of 1,1,3,3-tetramethyl-1,3-dihydroxy disiloxane.

3. The method as claimed in claim 1 wherein the mixture of the methyl dialkenyloxysilane and 1,1,3,3-tetramethyl-1,3-dihydroxy disiloxane is admixed with 50 to 1000 parts by weight of an organic solvent per 100 parts by weight of 1,1,3,3-tetramethyl-1,3-dihydroxy disiloxane.

4. The method as claimed in claim 1 wherein the reaction is performed at a temperature in the range from −10° to +80° C.

* * * * *